(12) United States Patent
Stuck et al.

(10) Patent No.: US 8,715,725 B2
(45) Date of Patent: May 6, 2014

(54) SECURE TRACKING OF TABLETS

(75) Inventors: Alexander Stuck, Wettingen (CH); Stefan Klocke, Karlsruhe (DE); Harald Walter, Zurich (CH)

(73) Assignee: I-Property Holding Corp., Sarasota, FL (US)

( * ) Notice: Subject to any disclaimer, the term of this patent is extended or adjusted under 35 U.S.C. 154(b) by 0 days.

(21) Appl. No.: 13/010,101

(22) Filed: Jan. 20, 2011

(65) Prior Publication Data
US 2011/0188051 A1    Aug. 4, 2011

Related U.S. Application Data

(63) Continuation of application No. PCT/US2009/051528, filed on Jul. 23, 2009.

(60) Provisional application No. 61/082,998, filed on Jul. 23, 2008, provisional application No. 61/226,941, filed on Jul. 20, 2009.

(51) Int. Cl.
*G01B 11/02* (2006.01)
*A61K 9/44* (2006.01)
*G01B 11/24* (2006.01)

(52) U.S. Cl.
USPC ........... 424/464; 356/511; 356/601; 424/10.2

(58) Field of Classification Search
None
See application file for complete search history.

(56) References Cited

U.S. PATENT DOCUMENTS

| | | | |
|---|---|---|---|
| 5,992,742 A * | 11/1999 | Sullivan et al. | 235/462.01 |
| 6,776,341 B1 | 8/2004 | Sullivan et al. | |
| 7,770,732 B2 | 8/2010 | Stroppolo et al. | |
| 2005/0261937 A1 | 11/2005 | Silverbrook et al. | |
| 2006/0068006 A1 | 3/2006 | Begleiter | |
| 2006/0206714 A1 | 9/2006 | Gubo | |
| 2006/0226234 A1 | 10/2006 | Kettinger et al. | |
| 2007/0086625 A1 | 4/2007 | Polli et al. | |
| 2007/0190133 A1 * | 8/2007 | Bunick et al. | 424/464 |
| 2007/0199991 A1 | 8/2007 | Haraszti et al. | |
| 2007/0219916 A1 * | 9/2007 | Lucas | 705/58 |
| 2007/0241177 A1 * | 10/2007 | Tuschel et al. | 235/375 |
| 2007/0286811 A1 * | 12/2007 | Walter | 424/10.2 |
| 2008/0042843 A1 | 2/2008 | Kim | |
| 2008/0199406 A1 * | 8/2008 | Walter et al. | 424/10.2 |
| 2010/0110514 A1 * | 5/2010 | Houha et al. | 359/2 |

FOREIGN PATENT DOCUMENTS

| WO | WO 2006/047695 | * | 5/2006 | A61J 3/00 |
|---|---|---|---|---|
| WO | WO 2007/137438 | * | 12/2007 | C90C 1/00 |

OTHER PUBLICATIONS

European Patent Office, International Search Report, Form PCT/ISA/210 (3 pgs.), and Written Opinion, Form PCT/ISA/237 (5 pgs.), Apr. 1, 2011, for PCT/US2011/22065.
International Search Report of PCT/US2009/51528, U.S. Patent and Trademark Office, Sep. 22, 2009.

* cited by examiner

*Primary Examiner* — Robert A Wax
*Assistant Examiner* — Danah Al-Awadi
(74) *Attorney, Agent, or Firm* — Wood, Herron & Evans, LLP

(57) ABSTRACT

The present invention relates to a verification method for tracking and tracing tablets, particularly pharmaceutical tablets. It further relates to a visible secure marking or information that is a part of such tablet (10). The invention further relates to tablets suitable for such verification method, processes for manufacturing such tablets, and methods for reading the information.

19 Claims, 2 Drawing Sheets

SECURE TRACKING OF TABLETS

RELATED APPLICATIONS

This application claims priority as a continuation under Section 120 and/or under Section 371 to International Application No. PCT/US2009/051528, entitled "Secure Tracking Of Tablets," filed on Jul. 23, 2009, which in turn claims priority to U.S. Application Ser. Nos. 61/082,998, filed on Jul. 23, 2008, and entitled "Secure Tracking of Tablets," and to 61/226,941, filed on Jul. 20, 2009, and entitled "Secure Tracking of Tablets," Each of these applications is incorporated by reference herein, in its entirety.

BACKGROUND OF THE INVENTION

The present invention relates to the secure tracking of pharmaceutical tablets, including the tablets themselves and methods for marking and verifying such tablets.

Pharmaceuticals and cosmetics are high technology products which require very specialized material systems and production procedures, as well as very large investments in development and marketing. Because of public safety concerns, authorities place very stringent requirements on the verification and authenticity of such products. Companies therefore have to make huge investments in the tracking and tracing of these products to ensure authenticity. In addition, because these products usually are distributed globally and have relatively large profit margins, cosmetics manufacturers and pharmaceutical companies suffer from and/or are susceptible to suffering from enormous losses due to counterfeiting. This includes direct losses due to lost sales, and also indirect losses due to the need to police trademarks, in order to protect the company's reputation. These problems have been aggravated by opportunities for increased sales over the Internet, where everything from counterfeit Viagra to false glucose tests seems to be readily available, anywhere.

Track-and-trace features in the pharmaceutical market are typically applied to packages. For example, holograms, optically variable inks, fluorescent dyes, and other identification features are attached to the packages, e.g., by adhesive tags. Alternatively, such labels are laminated to the carton or are directly applied to the packages. The main drawback of such labels is that they are not an integral part of the product or the packaging and therefore do not provide 100% security. And because the tablets themselves are not marked, they can be easily separated from the package, potentially leading to the refilling of the package with false products. Direct verification of the tablet, and ensuring that the authentic tablet is in the correct package are therefore primary concerns. Such track-and-trace procedures for the packages do not eliminate these concerns.

Further, few approaches are known for secure labelling of the tablet itself. And each of these tablet labelling approaches suffers from various drawbacks.

For instance, techniques based on forgery-resistant signatures, such as DNA of known sequence (U.S. Pat. No. 5,451,505) or molecules with characteristic isotopic composition or micro-particles with characteristic colour layer sequence (U.S. Pat. No. 6,455,157 B1), are considered unsuitable for pharmaceutical tablets, because these signatures are administered simultaneously and require additional regulatory approval.

Techniques based on a hologram on edible products are known. WO 01/10464 describes the coating of an edible product with a thermo formable and thus embossable layer. The tablets as disclosed in this document comprise a core, a coating, and a microstructure at the surface of said coating. The diffractive microrelief is visible to the unaided eye and exposed to mechanical stress, like abrasion. The microreliefs as described in this '464 application are generally considered to be very sensitive and thus susceptible to providing false results in verification methods. Still another drawback is that the methods for implementing the diffractive relief structure in such tablets, as described in this '464 application, are not considered compatible with the existing tablet mass production processes.

WO2006/027688A1 describes an article, such as a tablet, having a visible diffractive microstructure on its surface or at an interface. Illuminated with white light, the tablet shows a rainbow colour effect similar to a hologram. The diffractive microstructure can provide an indication of authenticity of the tablet. Although suitable for verification purposes, this '688 application discloses a security element that is visible to the unaided eye. Also, a relatively large area of the tablet needs to be covered by the microstructure to obtain good results regarding visibility.

A number of optical detection devices useful for analysing three-dimensional structures are known. White light interferometers are state of the art, but operate rather slowly. Optical coherence tomography (OCT) is another known technique capable of visualising three dimensional patterns, even if they are located at an interface below the surface of an article. The depth that can be visualised in a material depends on the optical properties of the material. Presently, that depth can be up to a few millimeters. U.S. Pat. No. 6,469,489 describes an array sensor which is used for parallel optical low-coherence tomography (pOCT) which enables real-time 3D imaging for topographic pattern. It provides fast, three-dimensional and structural information with spatial resolution in the micrometer range. This '489 patent does not disclose secure tracking of tablets. A plurality of electrical detection circuits with parallel outputs can form a one-dimensional or two-dimensional array sensor for the coherent or heterodyne analogue detection of intensity modulated optical signals simultaneously for all pixels with a high dynamic range. The array sensor may be used, e.g., for optical 3D measurements, and especially in optical low-coherence tomography. It is known to use OCT for investigating the human skin, to control the quality of fast production processes (e.g., in die-bonding), in SMD pick-and-place systems, as well as in mechanical inspection systems. Variants of these detection techniques do not use interferometry, but time-modulated optical signals to provide accurate 3D measurements of objects. Such variants often use parallel processing of lock-in signals on a single chip to provide fast and accurate distance information to an object. One example is time-of-flight (TOF) or related methods, where infrared or visible light from a camera's internal lighting source is time modulated and reflected by objects in the scene. The light travels back to the camera, where the time of arrival is measured independently by each pixel on a sensor array or chip. In contrast to conventional cameras, such cameras provide a complete distance map of all objects in the field of view on a pixel-by-pixel basis.

Altogether, there exists a need for the secure marking of tablets with security and tracking information, where the marking does not change the composition or the production process of the tablet, and can be easily read. There is also a need to link the marking information on the tablet to the package of the tablet, to reduce false delivery. Further, there is a need for a verification method that is contactless, fast, and reliable.

BRIEF SUMMARY OF THE DISCLOSURE

Thus it is an object of the present invention to mitigate at least some of these drawbacks of the state of the art. In particular, it is an aim of the present invention to provide an overt, i.e., visible, structure and method for tracking and tracing tablets through the production and supply chain. This is accomplished by marking the tablets themselves with an overt 2D or 3D code, by embossing or impressing, and linking the code to information on the package. Further, it is an aim of the present invention to provide a fast, optical verification method for such marked tablets, and a system using that verification method to determine the authenticity of such tablets, while avoiding the drawbacks of known or existing tablet verification methods.

The present invention is described in more detail below. It should be understood, to a person skilled in the art, that the various embodiments, preferences, and ranges may be modified and/or combined, as appropriate. Further, depending on the specific embodiment or application, some of the definitions, embodiments or ranges may not apply.

Unless otherwise stated, the following definitions apply in this specification:

The terms "tablet" or "pill" are known in the field. They relate in particular to a single solid dosage form comprising at least one solid active ingredient and optionally solid excipients (such as binders and other components). Tablets are usually manufactured by compacting, e.g., pressing, powders or granules of the respective components The term "active ingredient" ("a.i."), as used herein, is not limited to a "pharmaceutical active ingredient" but includes all kinds of ingredients that are active, such as flavours, fragrances, active ingredients for animal health, active ingredients for plant protection etc. Further, tablets may be coated, resulting in a tablet comprising a core and coating. Tablets are usually intended to be swallowed, or dissolved in water, and are therefore of a suitable size and shape for the purposes of the disclosed invention.

An "element of authenticity" or "topography pattern" comprises one or more predetermined three-dimensional structures. Its presence proves authenticity of a tablet or pill. Suitable structures are for example 2- or 3-dimensional bar codes, such as data matrix or pharma code, logos, symbols and the like.

A "predetermined three-dimensional structure" denotes any structure detectable by an optical device that can be measured and produced with an accuracy of better than 50 micros, preferred better than 10 microns.

A "verification method" is an optical method that allows distinguishing genuine articles, such as tablets or pills, from false articles.

BRIEF DESCRIPTION OF THE DRAWINGS

The Figures included with this specification are intended to further illustrate exemplary embodiments of the invention. These Figures are briefly described as follows.

DETAILED DESCRIPTION OF THE PREFERRED EMBODIMENTS

Figure 1:
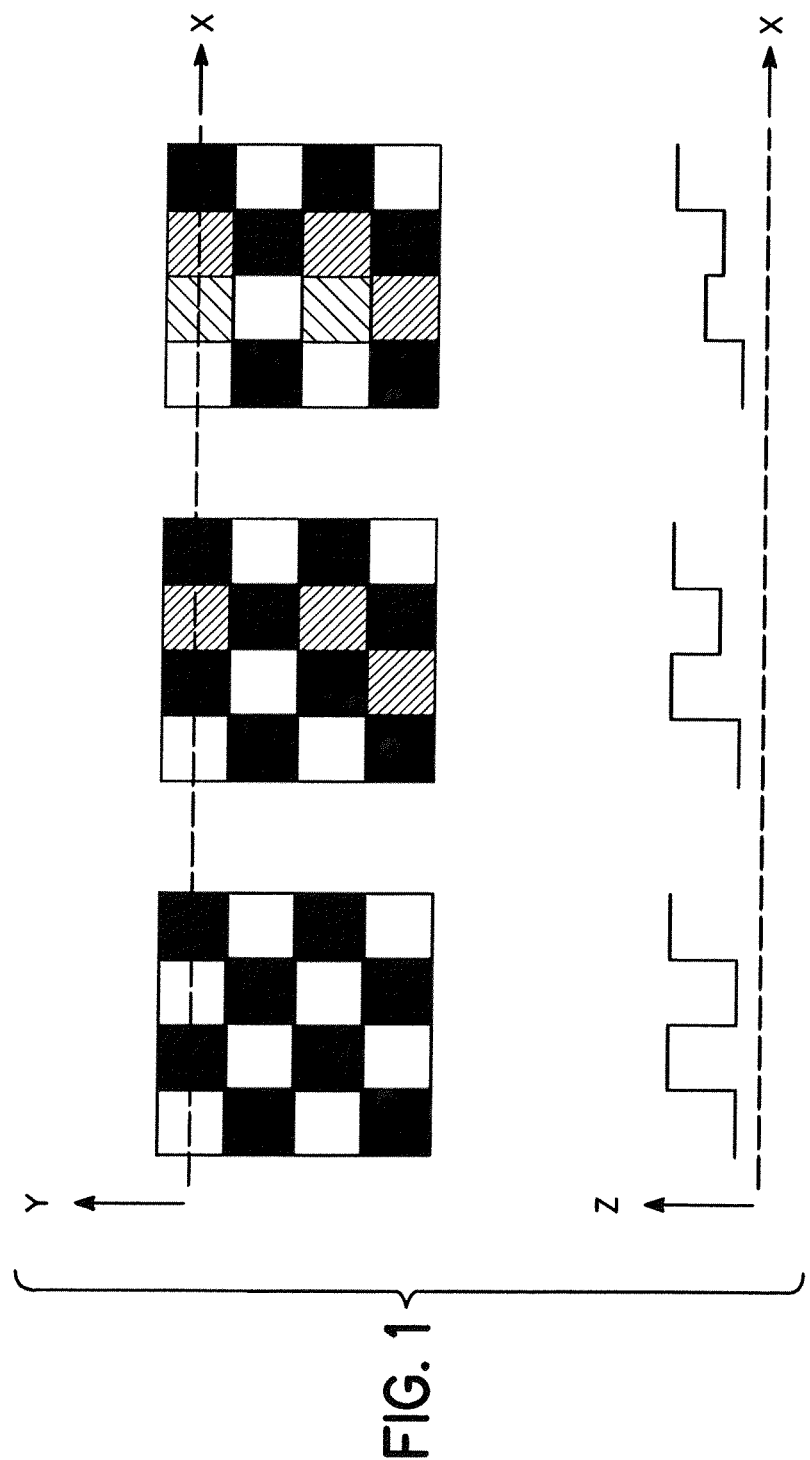
FIG. 1 is a schematic that shows an example of a 4×4 matrix code with different depth levels. At the upper portion of FIG. 1, the reference x/y denotes the plane of the surface or interface of the tablet, while the lower, aligned, portion shows that reference z is the direction perpendicular to this plane. The matrix on the left shows 2-levels: for example, a normal black/white 2D bar code. The matrix in the middle shows 3-levels, with two levels being the same code as 2-level code, but with an additional third level that contains a security code for authentication of the structure. The right matrix shows 4-levels: same as 2-level, but with levels 3 and 4 allowing the storage of additional product information on the same surface as the 2-level code.
Figure 2:
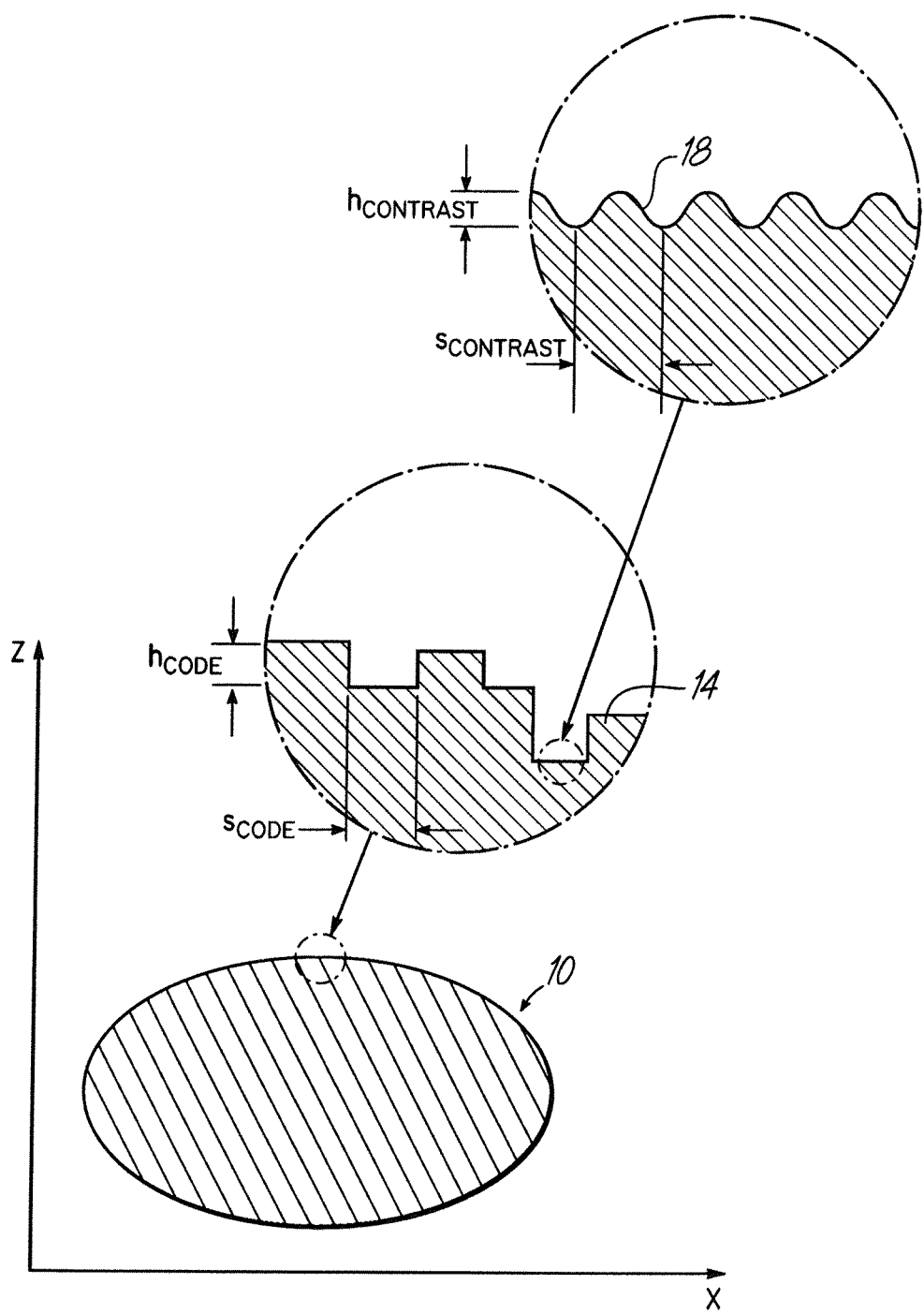
FIG. 2 is a schematic that shows the hierarchy of the embossed structures. A visible, rather large code structure with one or more depth levels is embossed into the pill surface during the manufacturing process. A much finer optical contrast structure—which is embossed together with the code structure—enhances the visibility of the code structure and provides additional security against counterfeiting. The smallest lateral structures size of the code structure is denoted as $s_{code}$, the vertical one $h_{code}$. The corresponding sizes of the contrast structure are denoted $s_{contrast}$ and $h_{contrast}$ respectively.

FIG. 1 shows three versions of a 4×4 matrix code, with 2, 3, and 4 levels. FIG. 2 schematically shows a tablet 10 with a code structure 14 formed in a surface thereof, and a contrast structure 18 formed within a portion of the code structure 14. As shown, the code structure 14 has features with square edges, while the contrast structure 18 has features with edges that form a sinusoidal pattern. Although not shown, those skilled in the art will readily appreciate that the structures 14, 18 may be covered with a transparent coating. Applicants expressly incorporate by reference herein, in its entirety, the disclosure of PCT Application No. PCT/US2005'038809, entitled "Dosage Forms Having A Microreliefed Surface And Methods And Apparatus For Their Production."

In a first aspect, an exemplary embodiment of the invention relates to a tablet or a pill comprising a combination of at least two three-dimensional structures on its surface or below an optically transparent coating (see FIG. 2) wherein the smallest feature of one predetermined structure, the code structure, is in the range of >10 μm up to 1 mm in lateral direction and >1 μm but <1 mm in vertical direction, and at least one contrast structure whose structure size is <5 μm in lateral direction and <3 μm in vertical direction, and wherein the smaller contrast structure makes an optical contrast either by modifying the surface reflectivity of the tablet or by diffraction, and at least the code structure is visible to the human eye. The whole code structure itself has typically a lateral dimension $ld_{code}$ of 50 μm×50 μm up to 10 mm×10 mm. Its shape is not necessarily square. Other shapes are possible as well. The code structure may carry information about the tablet, such as the name, the type of tablet, ingredients, date of production, etc. Suitable, preferred and especially preferred lateral and vertical structure sizes of the two structure types are listed in Table 1.

TABLE 1

|  | suitable range | preferred range | especially preferred range |
|---|---|---|---|
| $ld_{code}$ | 50 μm × 50 μm up to 10 mm × 10 mm | 500 μm × 500 μm up to 5 mm × 5 mm | 1000 μm × 1000 μm up to 2 mm × 2 mm |
| $s_{code}$ | 10 μm up to 1 mm | 30 μm up to 500 μm | 80 μm up to 300 μm |
| $h_{code}$ | 1 μm up to 1 mm | 2 μm up to 500 μm | 5 μm up to 50 μm |
| $s_{contrast}$ | 10 nm up to 5 μm | 100 nm up to 3 μm | 500 nm up to 2.5 μm |
| $h_{contrast}$ | 10 nm up to 3 μm | 100 nm up to 2 μm | 150 nm up to 600 nm |

In one advantageous embodiment, the information of the code is built into the depth profile of the code structure as well as the lateral distribution of the code structure, and the code is measured by an optical detection device capable of measuring 3D topologies.

In a further advantageous embodiment, the optical detection device is an optical 3D camera which uses time-modulated optical signals to accurately measure depth, such as an optical coherence tomography, optical time of flight, or similar device.

The term tablet is known in the field and already defined above. Some tablets consist of nearly 100% active ingredient (a.i.). Aspirin is one such example. In most cases typically, a tablet is a mixture of at least one active ingredient and excipients, usually in powder or granulated form, pressed into a solid dosage form. The mixtures consist of particles of different size, whereas the particle size distribution is considered critical for the compression process. A typical composition of such a powder mixture which is suitable for pharmaceutical tablets comprises 50-80% of a Lactose derivative (e.g. 73% Lactose Monohydrate), 10-50% of a cellulose derivative (e.g., 24% Microcrystalline Cellulose), 0.1-5% Silica, (e.g., 1% Aerosil (colloidal silica, anhydrous)), 0.1-5% of a fatty acid salt (e.g. 1% Magnesium-stearate) and 0.1-20% of a.i. (e.g., 1% a.i). Lactose and cellulose are the most widely used binding and filling agents, Aerosil improves the powder flow, and Mg-stearate is used as a lubricant. The particle size distribution of the powder is usually 15-25% smaller than 75 µm, 30-50% in the range of 75 µm-150 µm, 15-25% between 150 µm-250 µm, 5-15% between 250 µm-500 µm and less than 2% larger than 500 µm.

In a further advantageous embodiment, the invention relates to a tablet as defined above wherein the powder or granules used in the manufacturing are coated with a binding agent. Improvements in the plasticity of a powder can be achieved by coating the particle surface with a plastic material. For example the particles can be partially coated with a binding agent like polyvinylpyrrolidone (PVP), e.g., in wet granulation, which improves the compressibility of the particles. This, in turn, improves the quality of the three-dimensional structures embossed in the tablet.

A processed cellulose, microcrystalline cellulose, has been used extensively in the pharmaceutical industry as a direct compression vehicle for solid dosage forms. Microcrystalline cellulose is commercially available under the tradename "EMCOCEL®" from Edward Mendell Co., Inc., and as Avicel® from FMC Corp. Compared to other directly compressible excipients, microcrystalline cellulose is generally considered to exhibit superior compressibility and disintegration properties.

Suitable polymers for inclusion in top coatings include polyvinlyalcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivates such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene ocide and poylvinylpyrrolidone copolymers; polycinylpyrrolidone and polycinylacetate copolymers; and derivates and combinations thereof. Copolymers of acrylate and methacrylates with quarternary ammonium group in combination with sodium carboxymethylcellulose may also be used. Suitable film-forming water-insoluble polymers for inclusion in top coatings include for example ethylcellulose, carrageenan, polyvinyl alcohols, polyvinyl acetate, polycaprolactones, cellulose acetate and its derivates, acrylates, methacrylates, acrylic acid copolymers, and the like, and derviates, copolymers, and combinations thereof. Suitable film-forming pH-dependent polymers for inclusion in top-coatings include enteric cellulose derivates, such as for example hydroxypropyl methylcellulosephthalate, hydroxypropyl methylcellulose acetate succinate, cellulose acetate phthalate; natural resins, such as shellac and zein; enteric acetate derivates such as for example polycinylacetate phthate, cellulose acetate phthalate, acetaldehyde dimethylcellulose acetate; and enteric acrylate derivates such as for example polymethacrylate-based polymers such as poly (methacrylic acid, methyl methacrylate) 1:2, which is commercially available from Rohm Pharma GmbH under the tradename "EUDRAGIT S"; and poly(methacrylic acid, methyl methacrylate) 1:1, which is commercially available from Rohm Pharma GmbH under the tradename "EUDRAGIT L"; poly (butyl, methacrylate (dimethylaminoethyl)methacylate, methyl methacrylate), which is commercially available from Rohm Pharma GmbH under the tradename "EUDRAGIT E"; and the like, and derivates, salts, copolymers, and combinations thereof.

In one embodiment, the top coating includes coatings having a high rigidity, i.e., e.g., those coatings having a yield value sufficient to prevent deformation of the microrelief when exposed to normal manufacturing, handling, shipping, storage, and usage conditions. Suitable top coatings having high rigidity include film formers, such as for example, the high tensile strength film-formers well known in the art. Examples of suitable high tensile strength film-formers include, but are not limited to, methacrylic acid and methacrylate ester copolymers; polyvinylpyrrolidone; cellulose acetate; hydroxypropylmethylcellulose (HPMC), polyethylene oxide and polyvinylalcohol, which is commercially available from BASF under the tradename "Kollicoat IR"; ethylcellulose; polyvinyl alcohols; and copolymers and mixtures thereof.

In one embodiment, the top coatings may include the water-soluble high rigidity film formers selected from HPMC, polyvinylpyrrolidone, the aminoalkyl-methacrylate copolymers marketed under the trade mark "EUDRAGIT E" and copolymers and mixtures thereof.

In embodiments in which the dosage form is prepared via compression, suitable fillers include, but are not limited to, water-soluble compressible carbohydrates such as sugars, which include dextrose, sucrose, isomaltalose, fructose, maltose, and lactose, polydextrose, sugar-alcohols, which include mannitol, sorbitol, isomalt, maltitol, xylitol, erythritol, starch hydrolysates, which include dextrins, and maltodextrins, and the like, water insoluble plastically deforming materials such as microcrystalline cellulose or other cellulosic derivates, water-insoluble brittle fracture materials such as dicalcium phosphate, tricalcium phosphate, and the like and mixtures thereof.

In embodiments in which the dosage form is prepared via compression, suitable binders include, but are not limited to, dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum Arabic, tragacanth, pectin, Whelan, rhamsan, zooglan, methylan, chitin, cyclodextrin, chitosan, polyvinyl pyrrolidone, cellulosics, starches, and the like; and derivates and mixtures thereof.

In embodiments in which the dosage form is prepared via compression, suitable disintegrants include, but are not limited to, sodium starch glycolate, cross-lined polyvinylpyrrolidone, cross-linked carboxymethylcellulose, starches, microcrystalline cellulose, and the like.

In embodiments in which the dosage form is prepared via compression, suitable lubricants include, but are not limited to, long chain fatty acids and their salts, such as magnesium stearate and stearic acid, talc, and waxes.

In embodiments in which the dosage form is prepared via compression, suitable glidants include, but are not limited to, colloidal silicon dioxide, and the like.

In embodiments in which the dosage form is prepared via compression, the dosage form of the invention may also incorporate pharmaceutically acceptable adjuvants, including but not limited to preservatives, high-intensity sweeteners such as aspartame, acesulfame potassium, cyclamate, saccharin, sucralose, and the like; and other sweeteners such as dehydroalcones, grycyrrhizin, Moellin™, stevioside, Talin™, and the like; flavors, antioxidants, surfactants, and coloring agents.

In a further advantageous embodiment, the tablet comprises a pharmaceutically active ingredient ("pharmaceutical tablet" or "pill"). Pills are in particular subject to counterfeiting, and authentication devices are therefore of particular relevance.

The predetermined visible larger three-dimensional code structure may be any structure and is not limited to any periodicity or particular shape. Suitable are for example, alphanumeric characters, geometric figures, bar codes, in particular pharma code and data matrix code, logos, or combinations thereof. The three-dimensional code structure may be either an impression or a ridge or both. Impressed three-dimensional structures are preferred. These structures are superimposed by a smaller contrast structure, either fully or in part, which provides additional optical contrast and security against counterfeiting. The optical contrast structure is embossed or impressed at the same time as the predetermined larger structure. The optical contrast structure may be any structure whose average lateral structure size is smaller than 5 microns. It is not limited to any periodicity or particular shape. The optical contrast structure provides additional security against counterfeiting and enhances the visibility of the predetermined larger three-dimensional structure. This optical contrast structure reduces measurement errors of the larger three-dimensional code structure.

In an advantageous embodiment, the embossed contrast structure is a diffraction grating with a period between 500 nm and 2.5 micrometers and a grating depth between 150 nm and 600 nm. The grating shape can be rectangular, triangular, blazed, sinusoidal, quasi-sinusoidal, or combinations thereof.

In another advantageous embodiment, the embossed contrast structure is an optical antireflex structure which reduces surface reflectivity. Such antireflex structures have lateral structure sizes smaller than 600 nm's and structure depths between 60 nm's and 400 nm's. Typical examples are moth eye structures and antireflex gratings.

In another advantageous embodiment, the embossed contrast structure is a random or polycrystalline structure with lateral structure sizes smaller than 5 microns and a structure depth of more than 100 nm but less than 3 µm, which scatters light to provide optical contrast.

In an advantageous embodiment, the larger predetermined three-dimensional code structure is 50 µm to 5 mm in both lateral direction and 2 µm to 800 µm in vertical direction. These structure may possess two vertical levels or more (see FIG. 1). Structures of this size are detectable by an optical detection device, and are also visible to the unaided eye. Such tablets are easy to manufacture, fully comply with existing manufacturing processes, and can be distinguished from false products, e.g., by a method as described below.

In still another embodiment, the invention relates to a pill or tablet as described herein, wherein the combined code and contrast structures are located in a macroscopic depression of the pill or tablet such as macroscopic letters or logos and the like. By doing so the predetermined three-dimensional structures are protected from being abraded by e.g. mechanical contacts of tablets during the production process or by depowdering processes and the like. For example the combined structures can be embossed or impressed in the cross of the company Bayer, as it is used on Aspirin® tablets for instance.

In a second aspect, the invention relates to a verification and track-and-trace method for a tablet wherein the tablet comprises one or more three-dimensional code structures on its surface or below a coating, wherein the structure is visible to the unaided eye and wherein the method comprises the step of detecting the structure via an optical detection device. The three-dimensional code structure may be a predetermined structure, as described in connection with the first aspect of the present invention. Alternatively, the three-dimensional structure may be the structure obtained by a state-of the art manufacturing process for tablets. The information from the tablet is read by an optical verification device capable of measuring 3D topologies with a depth resolution of better than 30 microns within less than 8 seconds and verified electronically.

In an advantageous embodiment, the visible three-dimensional code structure contains a 1-, 2-, or 3-dimensional bar code, such as, but not limited to, a pharma or data matrix code. This code is read by an optical verification method as described above from the pill or table and compared to one or several additional data sets for verification. These additional data sets may also be, but do not have to be, on the pill or tablet or on the package of the pill. For example a step index code embossed into the pill with 3 or more distinguished height levels can contain several linked datasets; at most each level is a dataset of its own.

In a further advantageous embodiment, the additional data set is printed and/or embossed in/on the package of the pill, such as a blister, box, bottle, etc. Alternatively a label comprising the data set is stick to the package or it is applied by hot-transfer or lamination. The additional data set on the package is then compared with the data set from the pill or tablet to provide verification. For example, part of the data set on the pill contains a private cryptographic key that is used to unlock encrypted information on the additional data set on the package of the pill, or vice versa. In this way the system ensures that the pill actually is packed into the correct package, limiting the need to access external databases. To enhance security of the system, all data sets (on the package and on the pill) may be encrypted and be decrypted by the verification device before comparing and verifying the codes. In the case of a transparent and/or semitransparent package, such as a blister or bottle, this embodiment allows verification of the pill or tablet without opening the package. The method creates a direct link between the physical structure of the pill and information printed and/or embossed or otherwise marked on the package of the pill.

In a further advantageous embodiment, the additional data as well as encryption and description codes are stored in the verification device itself for verification.

Suitable optical detection devices are known in the field. In principle, any optical detection device capable of detecting three-dimensional structures as defined above is suitable. Preferred devices are selected from the class consisting of optical interferometry microscopes and time-modulated 3D cameras. They provide fast, three-dimensional and structural information with spatial resolution in the micrometer range.

A plurality of electrical detection circuits with parallel outputs can form a one-dimensional or two-dimensional array sensor for the coherent or heterodyne analogue detection of intensity modulated optical signals simultaneously for all pixels with a high dynamic range. The array sensor may be used, e.g., for optical 3D measurements, and especially in optical low-coherence tomography. Variants of these detection techniques do not only use time domain interferometry, but other time-modulated optical signals to provide accurate 3D measurements of objects. Such variants often use parallel processing of lock-in signals on a chip to provide fast and accurate distance information to an object. One example is by time-of-flight (TOF) or related methods, where infrared or visible light from a camera's internal lighting source is time modulated and reflected by objects in the scene. It travels back to the camera, where its time of arrival is measured independently by each pixel on a sensor array or chip. In contrast to conventional cameras, such cameras provide a complete distance map of all objects in the field of view on a pixel-by-pixel basis.

A portable or fixed verification system may combine several of the above-mentioned 3D measuring systems as well as standard 2D camera systems to verify the embossed code simultaneously or in a fast time sequence on the pill and/or on the pill and the package of the pill.

As the described secure marking or information is also used for tracking and product tracing, a verification method is needed. Such method is preferably fast (i.e., it takes less than one second to distinguish forged from unique tablets and read the information on the tablet).

In a further advantageous embodiment, the invention relates to a verification method as described above wherein the tablet is as defined in the first aspect of the invention. In a further advantageous embodiment, the invention relates to a verification method as described above wherein the tablet comprises a core and a coating and wherein the predetermined structure is located at an interface between the core and the coating and wherein the method comprises the step of detecting the structure through the coating. To apply the verification method to a coated tablet is considered particularly useful. Coated tablets are predominant on the market. The three-dimensional structure is protected against abrasion.

In a further advantageous embodiment, the invention relates to a verification method as described herein wherein the tablet is located in a blister. In this embodiment, verification of tablets takes place without unpacking the tablets. Blisters are typical packages for tablets, in particular pharmaceutical tablets. Thus, spot tests at distributors or pharmacies and the like are possible.

In a further advantageous embodiment, the invention relates to a verification method as described herein wherein the tablet is located in a blister and the optical detection device is a OCT, especially a pOCT. OCT is a suitable detection method, as standard blister packages are transparent in the visible to NIR region (typically between 400 and 900 nm). Therefore even packaged tablets can be verified by OCT.

In a further advantageous embodiment, the invention relates to a verification method for a tablet (in particular a tablet as defined herein) comprising the step of analysing (detecting and recording) the tablet by an interference microscopy and comparing the obtained data set with a predefined data set.

As the size of the powder particles of the tablet is predominantly in the range of 75 μm-500 μm the topography structure is superimposed on the grain structure of the particles. This has to be taken into account for the verification of the topography structure. FIG. 4 shows the grainy surface of a pharmaceutical tablet with a datamatrix code structure impressed in that surface. The picture was taken by scanning electron microscopy (SEM). The code structure is hardly seen due to the grainy surface of the tablets.

In an advantageous embodiment, the invention relates to a pill as described herein, wherein one or more identical predetermined three-dimensional structures as defined above are located on both sides of the pill. This ensures a reliable method of verification, as at least one face of the tablet will be in the direction of the optical detection device. This is particular suitable if tablets are verified through a blister package.

In an advantageous embodiment, the invention relates to a pill as described herein, wherein two different predetermined three-dimensional structures as defined above are located on each side of the pill. This ensures a reliable method to verify the orientation of the table in the package. This is particular suitable if tablets are verified through a blister package.

Methods to manufacture embossing or impressing tools for tablets or pill according to this invention are known in the art. Laser writing or e-beam lithography combined with dry etching are two possibilities. EP1958620A1 and WO2007144826A2 disclose another possibility based on photo lithography.

EXAMPLE

A topography pattern consisting of mirror-inverted datamatrix barcode was manufactured in a hard chromium-coated steel punch as follows: A thin light-sensitive layer of Microposit S1800 (Röhm & Haas) was spin-coated on the surface of the punch in a lab with no blue or UV light. The thickness of this layer was approximately 10000 nm. After deposition a soft bake at 100° C. for 15 minutes was carried out. Next the photo resist was exposed by a UV-lamp through a shadow mask with said datamatrix barcode. After the exposure the resist was developed in a bath with S303 (Microposit). Immediately after the development step the punch was put in a stop bath with pure water. The temperature of both baths was 30° C., and it was controlled to ±0.2° C. The opened mask was used to transfer the topography structure in the punch surface by a dry-etching step. This etching in the hard punch surface was done by bombardment with Argon ions (Veeco RF 350) with a kinetic energy in the order of 500 eV. At 500 eV the energy is low enough to prevent high penetration of the source ions into the sample but not to the detriment of etching efficiency. After the desired topography structure depth of 10 μm was reached the residual resist was removed leaving the clean punch surface with the topography structure.

This punch comprising the datamatrix code structure was modified to possess diffractive grating contrast structures on both levels—on top and in the depressions of the barcode—as follows:

1. A thin light-sensitive layer, a so-called "photo resist" named Ma-N440 (MRT) Microposit S1800 (Röhm & Haas), was deposited on the surface of the punch. Again, this was done in a special lab with no blue or UV light. The optimal thickness of this layer is in the range of 300 nm to 2000 nm. The deposition was be done by spray-coating (EFD Micro-Coat MC780S). After deposition a soft bake at about 100 for 30 minutes was carried out.

2. Next the photo resist was exposed in a holography setup by two interfering laser beams in such a way that a linear grating with a period of about 1500 nm was obtained. The integrated power was controlled by a photo diode. The laser was a HeCd Laser with a wavelength of 441.6 nm. More detail can be found in WO2007/144826A2 which is incorporated herein in its entirety.

3. After the exposure the resist was developed in developer S303 (Microposit). Immediately after the development step the tool was put in a stop bath with pure water. The temperature of both baths was 30° C., and it was controlled to ±0.2° C. At the end of the development step the photo-resist layer on top of the pill press tool had a grating with the desired period and depth.

4. To dry etch the grating in the tool surface a contrast in the etching rate of at least 2:1 must be implemented. To accomplish this, a metal chromium cap with a mass thickness of 100 nm was deposited on the ridges of the grating in the photo resist. To reach that goal the compressing tool with the developed photo resist layer was placed in a vacuum chamber (Balzers BAK550) such that the evaporated atoms cannot reach the troughs of the grating. The incidence angle of the chromium metal atoms was set to 6°.

5. Next the photo-resist layer was opened. The parts of the polymeric resist material without the chromium caps were etched in an O2-plasma (Oxford-RIE). The kinetic energy of the reactive oxygen ions was at about 500 eV.

6. The opened mask was used to transfer the grating structure in the tool surface by a further dry-etching step. This etching in the hard compressing tool surface was done by bombardment with Argon ions (Veeco RF 350) with a kinetic energy in the order of 500 eV. After the desired grating depth of about 300 nm was reached, the residual Cr and resist was removed leaving the clean micro-structured compression tool surface.

Manufacture of Tablets:

The punch as manufactured above was used in a rotary tablet press to manufacture tablets at a speed of about 30000 tablets per hour. The powder mixture used was 73% Lactose Monohydrate, 24% Microcrystalline Cellulose, 1% Aerosil (colloidal silica, anhydrous), 1% Magnesium-stearat and as active agent 1% Na-salicylat. Tablets were pressed with a compacting force on the order of 30 kN.

EP1958620A1 teaches a verification method based on three-dimensional structures such as barcodes or logos impressed or embossed in tablets, and in particular on pharmaceutical tablets. This '620 Application also discloses methods to manufacture tablet compression tools. This '620 patent application is incorporated herein by reference, in its entirety. The '620 Application does not mention the secure tracking of tablets nor is the combination of 3D-structures with contrast enhancing microstructures.

We claim:

1. A pharmaceutical tablet, comprising a surface defined by a single pressed mixture of at least one powdered or granulated ingredient, one or more predetermined three-dimensional structures on the surface, a contrast structure associated with the at least one predetermined three dimensional structure, and an optically transparent coating on the surface and covering said one or more predetermined structures,
wherein said predetermined structures are visible to the unaided eye and wherein said predetermined structures are detectable by an optical detection device measuring depth through said coating,
wherein said predetermined structures are embossed into the surface of the tablet such that the predetermined structures are defined by the surface defined by the single pressed mixture, and
wherein said predetermined structures and said contrast structure are simultaneously formed by embossing the surface of the tablet such that said predetermined structures and said contrast structure are defined by the surface defined by the single pressed mixture, and
wherein said predetermined structures and said contrast structure define relative dimensions to provide a macro/micro relationship, said predetermined structures having features defining a depth ranging from about 2 microns up to 500 microns and a transverse dimension ranging from about 30 microns up to 500 microns, and said contrast structure having features defining a depth and a transverse dimension, each of which is smaller than the depth and the transverse dimension, respectively, of the features of said predetermined structures.

2. A tablet adapted for increased security in tracking and tracing, comprising:
a surface defined by a single pressed mixture of at least one powdered or granulated ingredient;
at least one predetermined three dimensional structure formed in the surface by embossing the surface of the tablet such that said predetermined structures are defined by the surface defined by the single pressed mixture;
a contrast structure associated with the at least one predetermined three dimensional structure, wherein said predetermined structures and said contrast structure are simultaneously formed by embossing the surface of the tablet such that said predetermined structures and said contrast structure are defined by the surface defined by the single pressed mixture;
an optically transparent coating located at the surface and covering the at least one predetermined three dimensional structure,
wherein the at least one predetermined three dimensional structure is visible to the unaided eye and detectable by an optical detection device through the coating, thereby to facilitate overt tracking and tracing of the tablet, and
wherein said predetermined structures and said contrast structure define relative dimensions to provide a macro/micro relationship, said predetermined structures having features defining a depth ranging from about 2 microns up to 500 microns and a transverse dimension ranging from about 30 microns up to 500 microns, and said contrast structure having features defining a depth and a transverse dimension, each of which is smaller than the depth and the transverse dimension, respectively, of the features of said predetermined structures.

3. The tablet of claim 2, wherein the tablet is a pharmaceutical tablet.

4. The tablet of claim 2, wherein the footprint of the at least one predetermined three dimensional structure is in the range of about 50 microns×50 microns up to 10 mm×10 mm.

5. The tablet of claim 2, wherein the features of said predetermined structures have a depth ranging from about 5 microns to 50 microns, and a transverse dimension ranging from about 80 microns to 300 microns.

6. The tablet of claim 5, wherein the features of said contrast structure have a depth ranging from about 150 nanometers to 600 nanometers, and a transverse dimension ranging from about 500 nanometers to 2.5 microns.

7. The tablet of claim 2, wherein the at least one predetermined three dimensional structure comprises features having rectangular transverse cross sectional shape.

8. The tablet of claim 2, wherein the embossing of the at least one predetermined structure and the contrast structure is configured to be performed by a punch manufactured so as to have a desired micro-structured surface.

9. The tablet of claim 8, wherein the embossing of the at least one predetermined structure and the contrast structure is configured to be performed by applying a compacting force of about 30 kN.

10. The tablet of claim 2, wherein the formed structures are located in a macroscopic depression on the surface of the tablet, thereby to protect the structures from abrading.

11. The tablet of claim 2, wherein the embossing of the at least one predetermined structure is configured to be performed by a punch manufactured so as to have a desired micro-structured surface.

12. The tablet of claim 11, wherein the embossing of the at least one predetermined structure is configured to be performed by applying a compacting force of about 30 kN.

13. The tablet of claim 2, wherein the at least one predetermined three dimensional structure comprises features having rectangular transverse cross sectional shape and the contrast structure associated therewith comprises features having sinusoidal transverse cross sectional shape.

14. The tablet of claim 2, wherein the features of said contrast structure have a depth ranging from about 100 nanometers to 2 microns, and a transverse dimension ranging from about 100 nanometers to 3 microns.

15. The tablet of claim 2, wherein said contrast structure includes at least one of: a diffraction grating, an optical antireflect structure in the form of a moth eye structure or an antireflex grating, and a polycrystalline structure that scatters light to provide optical contrast.

16. The pharmaceutical tablet of claim 1, wherein the features of said contrast structure have a depth ranging from about 100 nanometers to 2 microns, and a transverse dimension ranging from about 100 nanometers to 3 microns.

17. The pharmaceutical tablet of claim 1, wherein the features of said predetermined structures have a depth ranging from about 5 microns to 50 microns, and a transverse dimension ranging from about 80 microns to 300 microns.

18. The pharmaceutical tablet of claim 17, wherein the features of said contrast structure have a depth ranging from about 150 nanometers to 600 nanometers, and a transverse dimension ranging from about 500 nanometers to 2.5 microns.

19. The pharmaceutical tablet of claim 1, wherein said contrast structure includes at least one of: a diffraction grating, an optical antireflect structure in the form of a moth eye structure or an antireflex grating, and a polycrystalline structure that scatters light to provide optical contrast.

* * * * *